United States Patent [19]

Augustyniak

[11] 4,188,944

[45] Feb. 19, 1980

[54] ACROMIO-CLAVICULAR RESTORATION BRACE

[76] Inventor: Marian Z. Augustyniak, 251 W. 81st St., New York, N.Y. 10024

[21] Appl. No.: 882,340

[22] Filed: Mar. 1, 1978

Related U.S. Application Data

[63] Continuation-in-part of Ser. No. 775,180, Mar. 7, 1977, abandoned.

[51] Int. Cl.² ............................................. A61F 5/40
[52] U.S. Cl. ......................................................... 128/94
[58] Field of Search ................ 128/94, 87 R, 83, 82; 224/11, 12, 22

[56] References Cited

U.S. PATENT DOCUMENTS

| 1,490,381 | 4/1924 | Gobar | 128/94 |
| 3,215,138 | 11/1965 | Groesbeck | 128/94 |
| 3,404,680 | 10/1968 | Gutman et al. | 128/94 |

FOREIGN PATENT DOCUMENTS

188606 7/1906 Fed. Rep. of Germany ............. 128/94

*Primary Examiner*—John D. Yasko
*Attorney, Agent, or Firm*—Karl F. Ross

[57] ABSTRACT

An acromio-clavicular restoration brace has a resilient but shape-retentive shoulder block having an arcuate concavity conforming to and adapted to rest upon the acromio-clavicular joint of a patient, the shoulder block being mounted on straps forming a harness which retains the block on the joint and applies a downward force to the block.

9 Claims, 9 Drawing Figures

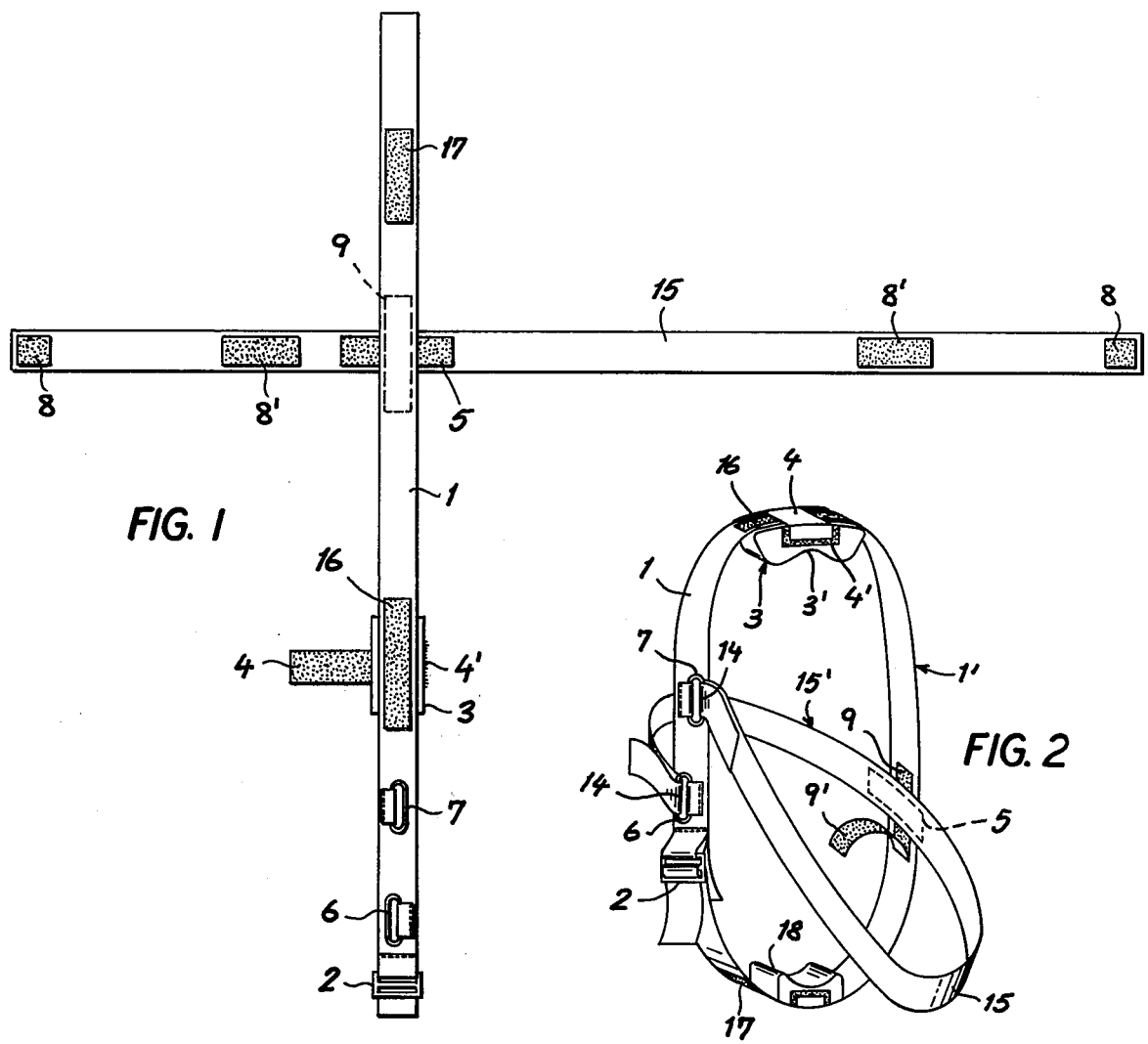
FIG. 1
FIG. 2
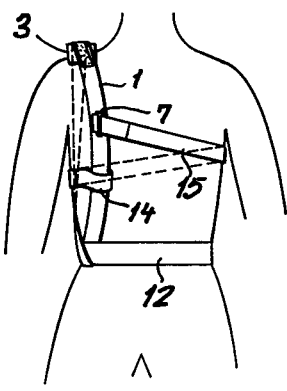
FIG. 3
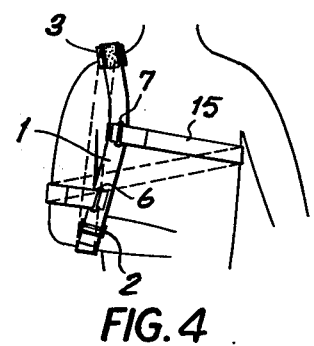
FIG. 4
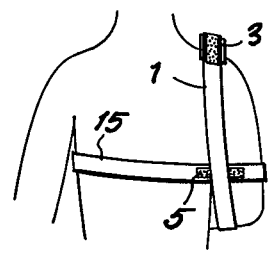
FIG. 5

ACROMIO-CLAVICULAR RESTORATION BRACE

This is a continuation-in-part application of my co-pending application Ser. No. 775,180 filed Mar. 7, 1977 and now abandoned.

FIELD OF THE INVENTION

The present invention relates, in general, to an orthopedic brace, and, more particularly, to an adjustable brace for restoring dislocated or broken clavicle and acromion bones to their proper position and to facilitate the healing of the injury.

BACKGROUND OF THE INVENTION

There are many instances in which it is desirable to treat a shoulder injury, such as a shoulder separation, with orthopedic devices. Such treatment may be preferred if the alternative is major surgery, or is otherwise impractical or undesirable.

Although there are devices for relocating the bones of the shoulder joint, such known devices often are not well suited for the treatment of shoulder separation or related injuries, as is evidenced by their relatively rare use in treatment of such injuries. Some of the drawbacks of the existing devices are that they may cause the formation of blisters, generally at the tip of the clavicle that is held down by the pressure applied by the device. The device also tends to cause skin abrasion and has rough surfaces in chafing contact with the patient's skin. Also, because of the design, construction and/or choice of materials such as abrasive surfaces, metal buckles and narrow leather straps in contact with the patient's skin, the existing device may inflict unnecessary pain and discomfort that may cause the patient to abandon the treatment.

Some existing devices, when applied, press down not only on the clavicle, as is desirable, but also on the scapula, thus forcing down also the acromion and preventing the separated bones from rejoining naturally. Tied to the elbow and lower arm with gutter-like holders, straps and buckles, some existing devices immobilize excessively the entire arm, preventing its exercise and thus contributing to atrophy of muscles and tissues.

OBJECTS OF THE INVENTION

It is therefore an object of my present invention to provide a brace for restoring broken or dislocated clavicle and acromion bones to their proper position.

It is another object of the present invention to provide a brace that will not cause skin irritation or abrasion when in contact therewith.

It is still another object of the present invention to provide a brace which is adjustable to prevent excessive downward pressure on the acromio-clavicular joint.

It is still a further object of my invention to provide a brace which will not excessively immobilize the arm of the patient.

It is yet another object of the present invention to provide a brace for the restoration of the acromio-clavicular joint which will be comfortable to wear.

SUMMARY OF THE INVENTION

The above and other objects of the invention are realized in a brace which can be worn directly on the body or over a garment. The clavicle is held down by means of a shape-retentive block of expanded synthetic resin or other, equivalent materials.

The block is attached, with means for adjustment, to an elastic shoulder strap material stretchable by tension and more or less vertical in relation to a standing patient. The shoulder strap of the harness extends over the shoulder, front and back, and forms a closed loop that is placed under the elbow to provide the downward force on the acromio-clavicular joint. The two ends of the shoulder strap are adjustably interconnected to shorten or elongate the loop.

In one embodiment of my invention, the looped strap is put over the shoulder as in conventional devices but is attached to a waist belt, such as the kind used to support trousers, or the like. The pressure and the holding force of the shoulder strap is set, adjusted and controlled with a continuously adjustable buckle or other means for this purpose. The shoulder strap, being of elastic material, absorbs changes in tension caused by body movements and thus reduces pain caused by sudden pressure increases, but maintains the tension, regardless of arm position. The vertical strap is adjusted and held in position by a perpendicular upper-body strap, fastened to the shoulder strap at the back of the patient with an adjustable attachement. One end of the upper-body strap is wrapped around the patient's chest and fastened to the shoulder strap in front. The other end of the upper-body strap is wrapped around the arm of the injured shoulder above the elbow, and also fastened to the shoulder strap in front. The fastenings may be a fabric of "hook and loop" type or other suitable means, located on the outside of the straps away from the body, to avoid causing discomfort by contact. The shoulder strap and the shoulder block can be positioned closer or farther away from the head, as is most beneficial for treatment, by the adjustment of each end of the upper-body strap at the shoulder-strap attachement. The upper-body strap around the arm, fastened to the shoulder strap, holds the arm close and more or less parallel to the body, but without excessive restraint, permitting exercise to avoid atrophy.

The device according to my invention eliminates or reduces the aformentioned limitations and adverse effects of existing devices by its design, materials, modes and methods of application. My improved device holds clavicle and acromion in the desired position without causing blisters since the pressure-applying pad is resilient and suitably shaped, and holding it are elastic straps which stretch and absorb excess pressure that might result in the formation of blisters. The shoulder block is held securely in place, without sliding and without contact with other areas of the skin.

The block, by its shape, prevents the top of the shoulder strap holding it from causing abrasions by rubbing and chafing the skin. The brace tension and positioning are continuously adjustable; the connections, adjustments, holding straps and all other projections are located on the outside surface, away from the body, and cannot cause pain or discomfort. Thus, the brace is more comfortable in use and more endurable through the time required for healing of the injury. The suitably thick and shaped shoulder block, extending beyond the shoulder to hold the top part of the shoulder strap away from the body, exerts pressure on the desired part only, without pressing down on the scapula which is thus free to be kept, along with the acromion, in an elevated position to meet the clavicle and re-form the damaged joint.

BRIEF DESCRIPTION OF THE DRAWING

The above and other features and advantages of my invention will become more readily apparent from the following description, reference being made to the accompanying drawing in which:

FIG. 1 is a plan view of the brace with the straps in an open, unlooped position;

FIG. 2 is a perspective view of the brace with the straps in a closed, looped position;

FIG. 3 is a diagrammatic front view of the brace in position on a patient, showing one feature of the invention;

FIG. 4 is a view similar to FIG. 3 showing another feature of the invention;

FIG. 5 is a rear view of the brace shown in FIG. 4;

SPECIFIC DESCRIPTION

Figure 6:
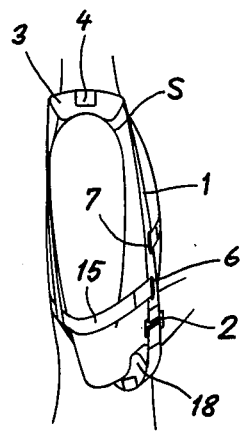
FIG. 6 is a side-elevational view of the brace shown in FIG. 4.

The acromio-clavicular restoration brace shown in FIGS. 1 and 2 is arranged for right-shoulder application and features a shoulder strap 1 made of an elastic material and provided with a friction buckle 2 at one end thereof for drawing the strap 1 into an adjustable loop.

An upper-body strap 15, also made of an elastic material, is provided at each end with a patch 8 of "hook and loop" fabric, which can be joined with another pair of "hook and loop" fabric strips 8', inwardly of the patches 8, to form loops 14 which engage eyes 6 and 7 provided on the front portion of the shoulder strap 1, the upper body strap 15 thereby defining an adjustable closed loop 15' transverse to the loop 1'. The strap 1 is further provided with a "hook and loop" fabric strip 16 on the outside of the loop 1' at the top and another such strip 17 on the outside of the loop 1' at the bottom, opposite strip 16. An additional "hook and loop" strip 9 is provided on the inside of loop 1', intermediate the strips 16 and 17, on the back portion, at the crossover point with the belt 15, which is provided on the outside of its loop 15' with a "hook and loop" strip 5 at that point, for the adjustable interengagement of the strips.

Figure 8:
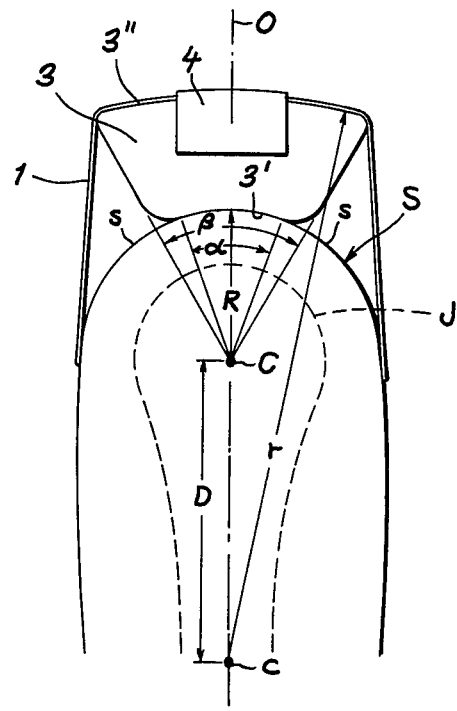
FIG. 8 is a side-elevational view, in diagrammatic form, of the shoulder block in position on the shoulder of a patient, showing the dimensional relationships thereof.
Figure 7:
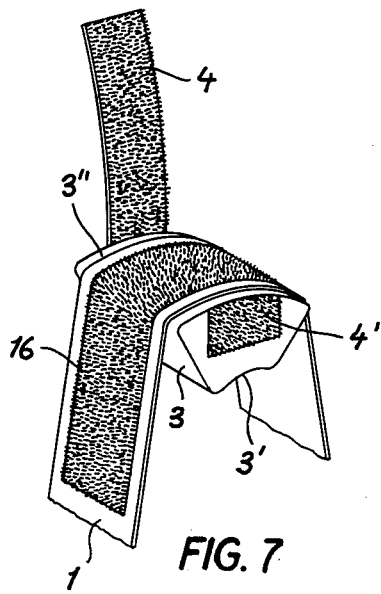
FIG. 7 is an enlarged detail view, in perspective, of the closure strip of the shoulder block.

A shoulder block 3 is provided inside the loop 1' at the top thereof and is adjustably secured to the strap 1 by a strip 4 of "hook and loop" fabric which is attached on one side of the block 3 and extends over the strap 1, engaging the strip 16 and another such strip 4' provided on the other side of block 3, which can be more clearly seen in FIG. 7. The block 3 is made of a resilient, shape-retentive material, such as foamed plastic, and is formed with an arcuate concavity 3' which engages the acromio-clavicular joint of the patient. The concavity 3', as best seen in FIG. 8, has a radius R equal to the distance from the center C of the ball-joint J of the shoulder S and an arc length with a subtended angle $\alpha$ ranging between 20 and 40 degrees. The top 3" of the block 3 is also arcuate, but to a lesser extent than the concavity 3', the arc 3" having a radius r 3.75 times that of radius R with a center c on the centerline O at a distance D below point C equal to 2R and an arc length with a subtended angle $\beta$ of 60 degrees causing the strap 1 to clear an area s on the shoulder S.

Figure 9:
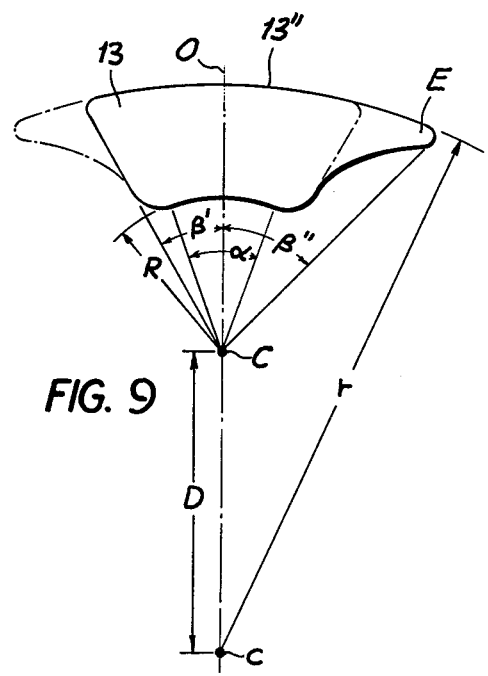
FIG. 9 is a view similar to FIG. 8 showing another form of shoulder block.

In the embodiment shown in FIG. 9, the shoulder block 13 has an extended portion E which can provide extra clearance for the strap 1 if so desired. All the dimensions of the block 13 are identical to those of block 3, with the exception of the arcuate top 13", which has an arc length with a subtended angle equal to $\beta'$, which is 30 degrees, pluse $\beta''$, which ranges between 30 and 45 degrees, and can be turned with the extension E facing front or back, depending on where the extra clearance is needed.

The shoulder strap 1 can also be provided with a forearm block 18, which is similar to the shoulder block 3 and is adjustably mounted on the strap 1 at the strip 17 in the same manner as the block 3.

In FIG. 3, the brace is shown in place on a patient with the shoulder strap 1 passing beneath and engaging the pants belt 12 of the patient, exerting the necessary downward force upon the shoulder block with the body strap 15 attached at one end to the eye 7 and passing around the chest and back of the patient while being attached to the strap 1 by the loop 14 passing around the strap, leaving the arm completely mobile.

FIGS. 4, 5 and 6 show the brace in place on the patient with the shoulder strap 1 passing under the forearm adjacent the elbow and one end of the body strap 15 secured to the eye 7 and passing around the chest and back and upper arm just above the elbow, limiting the mobility of the arm. At the crossover point of the straps 1 and 15 at the back of the patient, the strips 5 and 9 interengage to prevent relative movement between the straps, with a "hook and loop" strip 9' acting as a cover for the exposed parts of strip 9 not covered by the strap 15.

In operation, the shoulder strap 1 is placed on the patient with the shoulder block in position on the acromio-clavicular joint and the forearm resting on the lower block 18. The buckle 2 is then used to adjust the vertical tension in the strap 1; the blocks 3 and 18 are thereafter adjusted, if necessary, by repositioning along the respective strips 16 and 17. The strap 15, attached to the front of strap 1 by passing at one end through the eye 7 with the "hook and loop" patches 8 and 8' facing away from the body and forming a loop 14 which is adjustable by bringing the patch 8 against the strip 8' at different locations, is then passed around the chest and back to the crossover point with the shoulder strap 1, where it is adjustably attached by the strips 5 and 9 and then passed around the upper arm and secured to the strap 1 at the eye 6 in the same manner as at eye 7.

The same brace can also be used for left-shoulder application by detaching the strap 15, as seen in FIG. 1, from the strap 1, rotating it through 180 degrees and reattaching it to strap 1.

It should be pointed out that all the adjusting and attaching means shown are capable of being made by other means not shown, such as snap fasteners, for example.

I claim:

1. An acromic-clavicular joint-restoration brace comprising:
    a resilient shape-retentive shoulder block having an arcuate concavity conforming to and engaging with the body of a patient in the vicinity of the clavicle;
    strap means passing over the top of said shoulder block for securing said block in position on the joint to be restored and applying a downward force thereto; and fastening means for adjustably mounting said shoulder block on said strap means intermediate the ends thereof;

said top of said shoulder block extending beyond the ends of said arcuate concavity for keeping said strap means spaced apart from the shoulder of the patient.

2. The brace according to claim 1 wherein said top of said shoulder block extends farther beyond one end of said concavity than the other for keeping said strap means spaced apart from the shoulder of said patient over a greater distance on one side than the other.

3. The brace according to claim 1 wherein said strap means comprises:

an elastic shoulder strap passing over said shoulder block with closure means at one end thereof for adjustably securing the other end thereto to form a first loop extending downwardly from said shoulder of said patient along the front and back thereof;

an elastic upper-body strap transverse to said shoulder strap, said upper-body strap having ends adjustably secured to the front portion of said shoulder strap to form a second loop passing around the upper body of said patient; and means retaining for adjustably securing said upper-body strap intermediate the ends thereof to the back portion of said shoulder strap.

4. The brace according to claim 3, further comprising a resilient shape-retentive forearm block having an arcuate concavity conforming to and engaging with the forearm adjacent the elbow of said patient with holding means for adjustably mounting said forearm block on said shoulder strap opposite said shoulder block in said first loop.

5. The brace according to claim 3 wherein said shoulder strap passes under the pants belt of said patient to capture said belt in said first loop for exerting said downward force upon said shoulder block.

6. The brace according to claim 3 wherein said shoulder strap passes under the forearm adjacent the elbow of said patient to capture said forearm in said first loop for exerting said downward force upon said shoulder block and said upper-body strap passes around the upper arm adjacent the elbow of said patient to capture said upper arm in said second loop for limiting the mobility thereof.

7. The brace according to claim 4 wherein said shoulder strap bearing said forearm block passes under said forearm with said forearm block engaging said forearm in said first loop for exerting said downward force upon said shoulder block and said upper-body strap passes around the upper arm adjacent the elbow of said patient to capture said upper arm in said second loop for limiting the mobility thereof.

8. The brace according to claim 1 wherein said arcuate concavity has a radius equal to the distance from the center of the ball-joint of the shoulder of said patient to the point of engagement of the acromio-clavicular joint with said concavity, said arcuate concavity having an arc length with a subtended angle ranging between 20 and 40 degrees, said top of said shoulder block being arcuate and having a radius equal to substantially 3.75 times the radius of said concavity and an arc length with subtended angle ranging between 60 and 75 degrees, said top of said shoulder block having a center of curvature lying on a line at a distance substantially twice the radius of said concavity below the center of said ball-joint, said line being the bisector of said arcuate concavity.

9. The brace according to claim 4 wherein:

said closure means is a friction buckle mounted at said one end;

said fastening means includes an area of "hook and loop" fabric provided on the outside of said first loop in the region of said shoulder and said shoulder block is provided on one side with an area of "hook and loop" fabric and on the other side with a closure strip lined with "hook and loop" fabric for passing over and engaging with the "hook and loop" fabric on said first loop and the "hook and loop" fabric on said one side of said shoulder block;

said holding means is identical to the mounting of said shoulder block; and said retaining means includes an area of "hook and loop" fabric provided on the inside of said first loop intermediate said shoulder block and said forearm block and an area of "hook and loop" fabric provided on the outside of said second loop intermediate the ends thereof and engaging the "hook and loop" fabric of said first loop.

* * * * *